United States Patent [19]

Song et al.

[11] Patent Number: 5,528,653

[45] Date of Patent: Jun. 18, 1996

[54] ROTATIONAL CONIFORMLY-FOCUSED GAMMA RADIATING UNIT

[76] Inventors: Shipeng Song; Yixiang Su; Yi Du, all of P.O. Box 137 Room 1701-3 World Trade Centre, Shenzhen, Guangdong, 518014, China

[21] Appl. No.: 351,330

[22] PCT Filed: Apr. 8, 1994

[86] PCT No.: PCT/CN94/00025

§ 371 Date: Feb. 3, 1995

§ 102(e) Date: Feb. 3, 1995

[87] PCT Pub. No.: WO94/24443

PCT Pub. Date: Oct. 27, 1994

[30] Foreign Application Priority Data

Apr. 13, 1993 [CN] China ........................ 93103858.8
Dec. 21, 1993 [CN] China ........................ 93235783.0

[51] Int. Cl.⁶ ........................................... A61N 5/10
[52] U.S. Cl. ........................... 378/65; 378/119; 378/147; 378/149
[58] Field of Search ....................... 378/65, 149, 147, 378/119

[56] References Cited

U.S. PATENT DOCUMENTS 4,233,519  11/1980  Coad ............................ 378/65
4,780,898  10/1988  Sundqvist ...................... 378/65
5,267,294  11/1993  Kuroda et al. ................. 378/65

FOREIGN PATENT DOCUMENTS 2672220   8/1992   France.

OTHER PUBLICATIONS

"Stereotactic Radiosurgery", Forster and Dias, Surgery, No. 97, Oct. 1, 1991, pp. 2323–2325.

*Primary Examiner*—Craig E. Church
*Attorney, Agent, or Firm*—Ladas & Parry

[57] ABSTRACT

The present invention provides a rotator Gamma radiation unit which adapts to medical Gamma systems especially. The radiation source bodies carrying sources can rotate by 360° within a radiation protection case. The trace of the radiation line forms several rotating pyramids with tops at the common focus. In this way the single successive radiation in the stationary focus manner is changed to multiple-points intermittent radiation. Therefore, while ensuring the radiation amount, it is possible to decrease the number of the radiation sources and simplify the manufacturing engineering. In this way it is possible to kill the disease tissues at the focus, and prevent the nuclear radiation line from injuring the healthy tissues outside the focus.

10 Claims, 3 Drawing Sheets

ROTATIONAL CONIFORMLY-FOCUSED GAMMA RADIATING UNIT

TECHNICAL FIELD

The present invention relates to a radiating unit of Gamma cutter system, and more particularly, to a rotable Gamma-ray radiating unit.

BACKGROUND OF THE INVENTION

The existing Gamma-ray radiating unit, as a key component of a medical device used in nuclear actinotherapy-Gamma cutter system, in regard to its configuration, includes a source body consisting of a number of radiation sources, and the source body is mounted in an antiradiation protection shielding case with its beam channels being directed radically toward a common focal point, such as what is described in European Patent Publication EP-248774. Since the Gamma cutter employs multiple radiation sources each with only a small dosage of radiation, it provides the maximum radiation energy only at the common focal-point, so that the tissue with pathological changes at the focal point will be effectively killed without any harm to its surrounding healthy tissues in certain period of time. Based on this consideration, the existing Gamma-ray radiation unit uses as many radiation sauces as possible, for example, in Leksell Gamma Cutter produced by Swedish ELEKTA Company, there are 201 radiation sources arranged regularly on a hemisphere. With quite a number of radiation sources and the correspondingly increased use of heavy metallic shielding materials, both the weight and the volume of such Gamma cutter will be enormous. In terms of manufacturing, to orderly and accurately make hundreds of holes having a common focal point on a hemisphere with quite a large diameter calls for rigorous technical measures and technological equipment. And since the source body is fixed in the shielding case, and its Gamma rays, even with smaller radiation energy, statically focus on the tissue of pathological changes, still needing to continuously get through healthy tissues to reach the focus of infection, harms will inevitably be caused to healthy tissues due to the progressive accumulation of radiation time.

DISCLOSURE OF THE INVENTION

The object of the present invention is to provide a rotational coniformly-focused Gamma-ray radiation unit with a simple configuration and less radiation sources, so as to ensure effective beam radiations and reduce harms to healthy tissues.

The task of the present invention is accomplished in the following way: the source body of the rotational coniformly-focused Gamma-ray radiating unit is a geometrical solid of revolution symmetrical to the central axis of the radiating unit, several radiation sources and beam channels are set up in the source body to radially aim at a common focal point inside the shielding case and around the common focal point there is at least a space enough for a human brain. The antiradiation protection shielding case is provided with a rotable mandrel which is on the central axis of the radiating unit with one end fixed to a mandrel base of the source body and the other end linked with a drive device. Because the source body is fixed to the rotable mandrel, under power-driving, the source body can rotate by 360° within the antiradiation protection shielding case. In the operating state, the scanning traces of the beams of radiation sources of the source body thus form several conical surfaces or pyramids with the common focal point as a common apex. When all beam channels are not symmetrical to the mandrel, the scanning trace of each beam of the source body will form an independent revolutionary conical surface; if these revolutionary conical surfaces are sectioned by some planes perpendicular to the axis of rotation, the traces on the planes would be some concentric circles with different radii and the common focal point as a center. It can be seen thereby that, no matter the source body remains stationary or dynamically rotative, the beam radiation which the common focal point accepts is continuously constant. However, a beam-scanned point out of the common focal point only accepts a single instant irradiation intermittently during a revolution of the source body, and its irradiation time is significantly shorter than that of the common focal point. Therefore, with the effect of the rotating source body, the number of radiation sources can be reduced while correspondingly the filling dosage of every radiation source can be increased to provide for the total radiation energy. In the practical process of medical treatment, the tissue with pathological changes at the focal point can be effectively killed, without any harm to healthy tissues out of the focal point.

The radiating unit of the present invention adopts a dynamically focusing means to replace statically focusing means used in the prior art, its viewpoint does not lie in increasing radiation source and dispersing radiation dosage to reduce harms to healthy tissues, but in changing the existing continuous single-point radiation of each beam into multi-point radiation. Thus the single-point radiation time can be reduced to enhance the safety of healthy tissues during the process of medical treatment. Since the source body has such a revolutionary configuration, the number of radiation sources and the use of heavy metal materials are decreased, the manufacturing process is significantly simplified and the weight and volume of the product are correspondingly reduced to directly lower the production cost.

BRIEF DESCRIPTION OF THE DRAWINGS

In the following, further description will be made in combination with attached drawings in which.

BEST MODE FOR CARRYING OUT THE INVENTION

Figure 1:
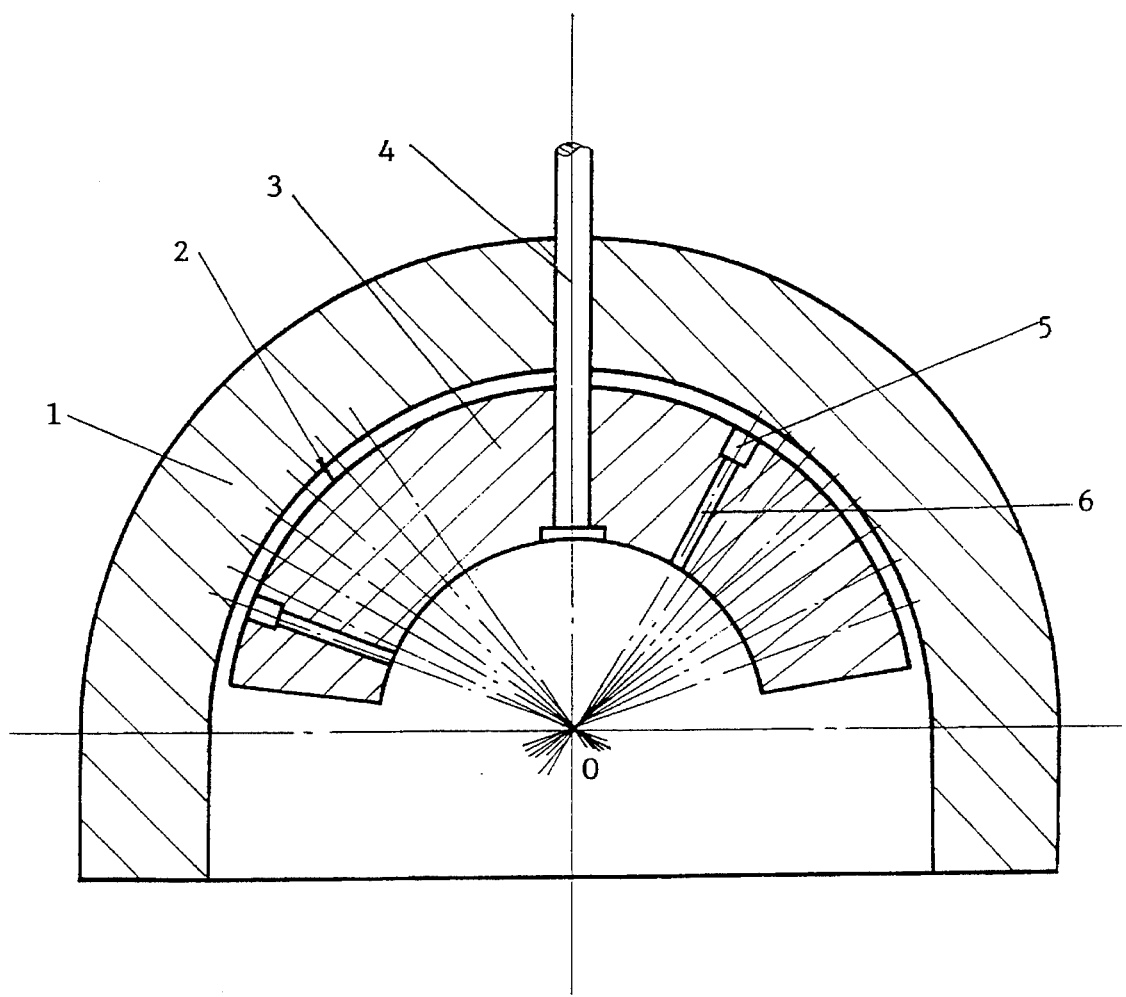
FIG. 1 is the structural schematic view in section of an embodiment of the radiating unit in accordance with the present invention.

Referring now to FIG. 1, a source body 2 of the embodiment is a sectarial plate-shaped body extending along both sides of mandrel base 3, radiation sources 5 and beam channels 6 are arranged along the sectorial curved surface of the plate-shaped body. This source body configuration has less radiation sources suitable to the radiation applications with smaller dosages.

Figure 2:
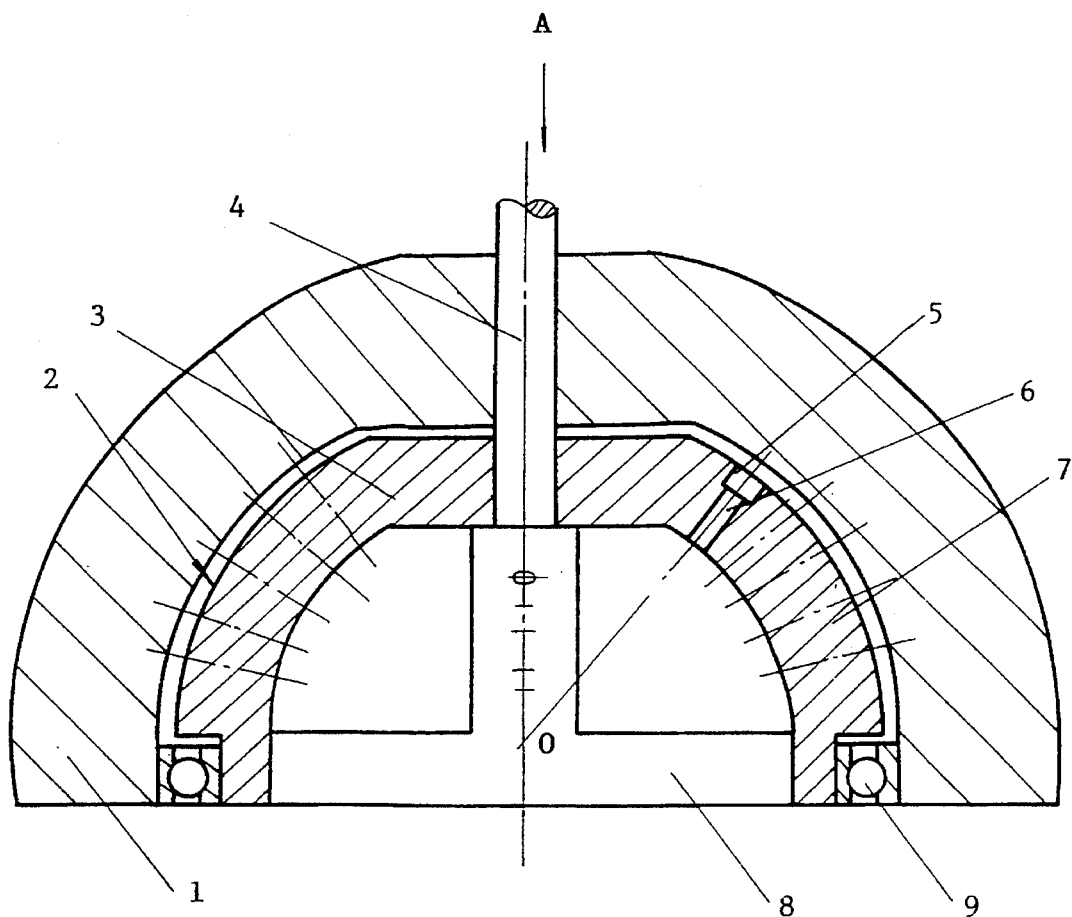
FIG. 2 is the structural schematic view in section of another embodiment of the radiating unit in accordance with the present invention.
Figure 3:
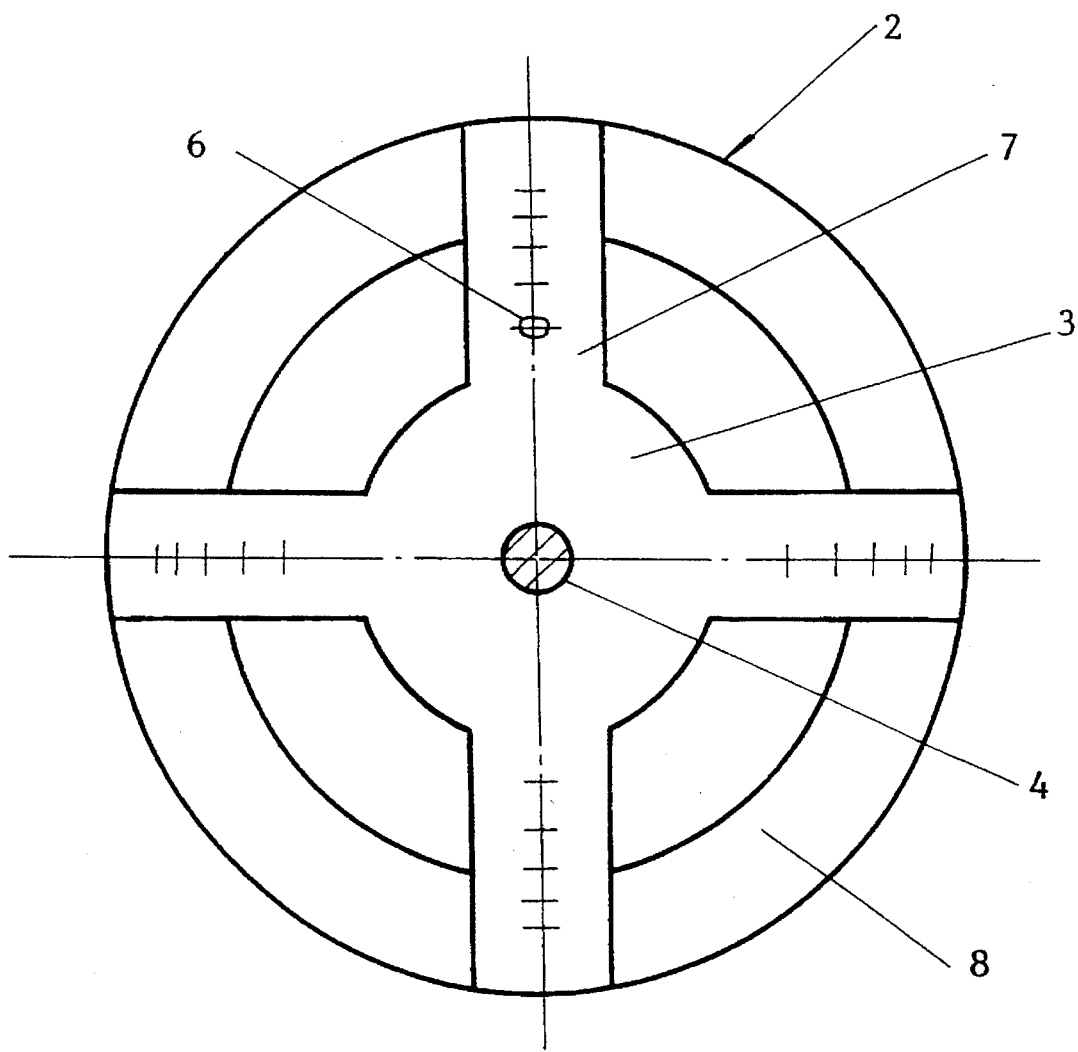
FIG. 3 is a view of the source body portion in the direction drown by arrow A in FIG. 2.

FIG. 2 and FIG. 3 show the second embodiment of the invention. A source body 2 of this embodiment is an open hemispheric frame composed of a mandrel base 3, an annular support 8 and several source body brackets 7 which extend radially along the mandrel base 3 and connect with the annular support 8 located at the bottom of source body 2. The radiation sources 5 and beam channels 6 are arranged along source body brackets 7. The source body configuration provides structurally a large space for rational disposition of radiation sources, and also has more universality.

Referring to FIG. 1 and FIG. 2, in the embodiments of the present invention, the source body 2 is accommodated in an antiradiation protection shielding frame or shielding case 1 which is of a hollow hemispheric configuration wholly formed by the materials such as cast iron or steel to provide for its desirable shielding performance. A mandrel 4 is located on the central axis of the radiating unit, adopting running fit with the antiradiation protection shielding case 1, and in order to ensure the mandrel to rotate with higher precision, it is preferable to use sliding bearing or the combination of sliding bearing and rolling bearing between the shielding case 1 and mandrel 4. The outer end of mandrel 4 is connected to a drive device which can be directly mounted on the casing of shielding case 1. In the present invention, the requirements to the drive system lies in that enough starting torque and uniform transmission can be ensured and the revolutionary focusing function can be achieved when the source body normally rotates in the lower speed state. In the embodiment of the present in venation, there have been employed a DC tachomotor drive and worm gear redactor transmission, and source body 2 rotates uniformly at a lower speed of 2~10 rpms. The mandrel 4 and the source body 2 are installed by use of interference fit, with the central line of mandrel 4 aiming at the common focal point 0. The whole source body 2 is formed by casting with materials such as cast iron or cast steal, and there is only a very small space kept between its outer circumference and the inner circumference of the shielding case 1 to ensure the shielding effectiveness. The space kept inside the source body 2 should be large enough to accommodate a human body's brain as it rotates.

The flame-type source body configuration shown in the embodiment of FIG. 2 and FIG. 3 has four source body brackets 7 mutually crossed and symmetrical to the mandrel base 3. The source body 2 is composed of the mandrel base 3, source body brackets 7 and annular support 8 to be an integral component, having desirable structural integrity. The annular support 8 is linked with antiradiation protection shielding case 1 by a bearing 9 in between, which is preferably a large diameter ball bearing with the aim of enhancing the structural stability and improving the rotation performance of the source body.

In the embodiments of the present invention, drilled in source body 2 are mounting holes used for mounting radiation sources 5 and beam channels 6, the requirements to these mounting holes are: firstly, the extended central lines of all holes must converge accurately on the common focal point; secondly, these holes are all not symmetrical to the central axis to ensure the scanning trace of each single beam not to be in coincidence; thirdly, when viewed from a radial plane of source body 2, the mounting holes are distributed outside the section which forms two 30° sectors on both sides of the mandrel axis so as to avoids the radiation sources 5 and beam channels 6 to be excessively close to mandrel 4, for avoiding nearly static radiation to be caused due to too small radii of revaluation. To ensure the machining accuracy and to meet distribution requirement of the mounting holes, numeral control machine tools can be used to do machine-work. The beam channels 6 are elongated sleeves made of heavy metal materials, at their upper ends there are cavities for filling with the radiation sources 5, and the beam channels 6 are inserted into the mounting holes of the source body 2 by transition fit. The amount of radiation sources 5 is determined in accordance with the minimum radiation energy needed to kill the tissue with pathological changes on the focal point 0 and maximum filling dosage with which a single radiation source will not cause any harms to healthy tissues under the rotative state. Also, the rotation of the source body about the axis has to be considered; since the radiation sources close to the axis of rotation are with smaller beam scanning radii and lower linear velocities and the radiation sources away from the axis of rotation are with larger scanning radii and higher linear velocities, to obtain a dosage field with uniform radiation, it is necessary to accordingly vary the filling dosages of the radiation sources. The source body configuration provided by the present invention ensures the radiation source disposition according to the distribution requirement to the dosage field of the rotating source body, causing a dosage field with uniform radiation.

We claim:

1. A Gamma-ray radiation unit comprising a source body being rotatable about a central axis of the radiation unit and having a central mandrel base and a plurality of radiation sources and radiating beam channels radially disposed around the source body, said source body defining a space capable of accommodating a human head, a rotatable mandrel disposed along the central axis and having one end fixed on said mandrel base, an antiradiation protective shielding case on which the mandrel is mounted so that the source body is rotatably disposed in said protective shielding case, said radiation sources through said beam channels radially aiming at a common focal point within said space of the source body inside the protective shielding case, and a driving device connected to the other end of the mandrel, that extends outside the protective shielding case, to rotate the source body.

2. The radiation unit according to claim 1, wherein said source body includes a sectorial plate-shaped body radially outwardly extending from the central mandrel base, said radiation sources and said beam channels being arranged along the sectorial plate-shaped body of the source body.

3. The radiation unit according to claim 2, wherein said radiation sources and said beam channels in the source body are symmetrically distributed outside a section which forms a 300° sector with respect to the central axis around the mandrel.

4. The radiating unit according to claim 2, wherein said radiation sources and said beam channels are not symmetrical to the central axis of the radiating unit.

5. The radiating unit according to claim 1, wherein said source body is an open hemispheric frame composed of the central mandrel base, an annular support located at the outmost rim of the source body, and a plurality of source body brackets which extend radially outwardly from the mandrel base and connect with the annular support, said radiation sources and said beam channels being arranged along the source body brackets.

6. The radiating unit according to claim 5, wherein said radiation sources and said beam channels in the source body are distributed outside a section which forms a 300° sector with respect to the central axis around the mandrel.

7. The radiating unit according to claim 5, wherein said radiation sources and said beam channels are not symmetrical with respect to the central axis of the radiating unit.

8. The radiating unit according to claim 5, wherein said plurality of source body brackets include four source body brackets mutually crossed and symmetrical to the mandrel base.

9. The radiating unit according to claim 5, wherein said mandrel base, the source body brackets and the annular support form an integral component.

10. The radiating unit according to claim 5, wherein a bearing is provided between said annular support and said protective shielding case.

* * * * *